United States Patent [19]
Carlson et al.

[11] Patent Number: 5,376,163
[45] Date of Patent: Dec. 27, 1994

[54] FILTER SYSTEM

[75] Inventors: Lee R. Carlson, Pleasanton; Eric L. Kewley, Alameda; Mahmoud Janbakhsh, Sunnyvale; Diane M. Battilana, San Leandro, all of Calif.

[73] Assignee: Andros Incorporated, Berkeley, Calif.

[21] Appl. No.: 63,151

[22] Filed: May 18, 1993

[51] Int. Cl.$^5$ .................... B01D 29/00; B01D 35/01
[52] U.S. Cl. .......................... 95/22; 95/23; 95/273; 55/215; 55/219
[58] Field of Search .......... 95/19, 22, 23, 273, 95/291; 55/210, 212, 215, 218, 219

[56] References Cited

U.S. PATENT DOCUMENTS

| | | | |
|---|---|---|---|
| 3,416,547 | 12/1968 | Glenn, Jr. et al. | 95/19 X |
| 4,113,450 | 9/1978 | Goransson et al. | 95/19 |
| 4,355,652 | 10/1982 | Perkins | 55/219 X |
| 4,592,368 | 6/1986 | Ricciardelli et al. | 55/215 X |
| 4,687,934 | 8/1987 | Parnoff et al. | 250/343 |
| 4,704,140 | 11/1987 | Kujala | 95/19 |
| 4,730,634 | 3/1988 | Russell | 95/22 |
| 4,906,257 | 3/1990 | Fukunaga et al. | 95/19 |
| 4,976,750 | 12/1990 | Munari | 95/19 |
| 5,049,170 | 9/1991 | Parnoff | 55/323 |
| 5,096,598 | 3/1992 | Pecen et al. | 55/218 X |
| 5,122,167 | 6/1992 | Daniels | 95/273 |
| 5,163,979 | 11/1992 | Patrick et al. | 95/19 |

*Primary Examiner*—Robert Spitzer
*Attorney, Agent, or Firm*—McCubbrey, Bartels & Ward

[57] ABSTRACT

A method and system are described for preventing flooding of a gas analyzer of the type wherein a pump conveys gas to be analyzed to a sample cell and a filter separates water from the gas flowing to the pump. The presence of excess liquid in the system is sensed by a pressure transducer which decouples the output of the pump from the sample cell and feeds it back to the filter. This results in an increase in pressure in the filter to prevent excess liquid from flooding the gas analyzer. The pressure is so held until the excess liquid passes from the filter system, after which the system returns to normal operation.

18 Claims, 2 Drawing Sheets

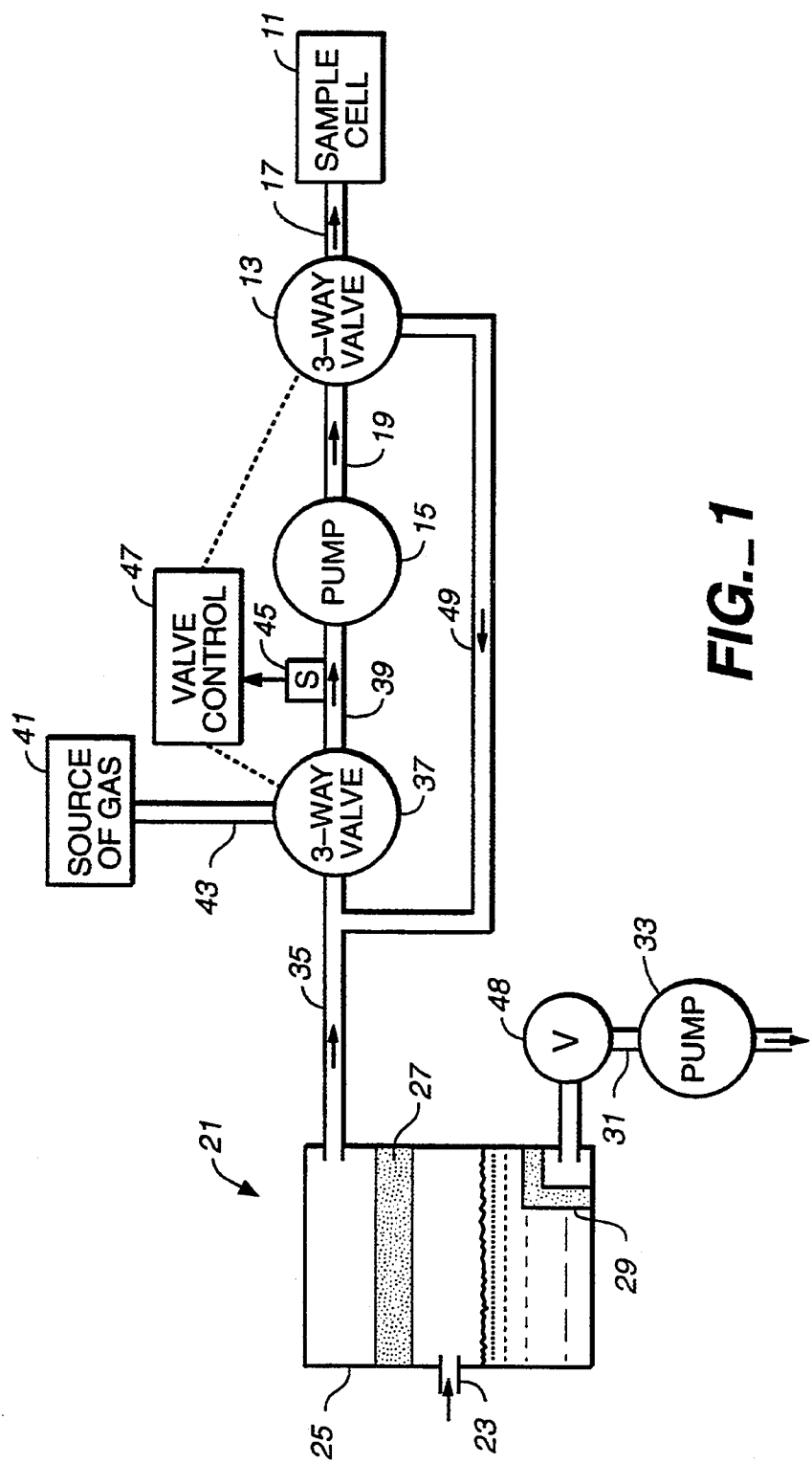
FIG._1

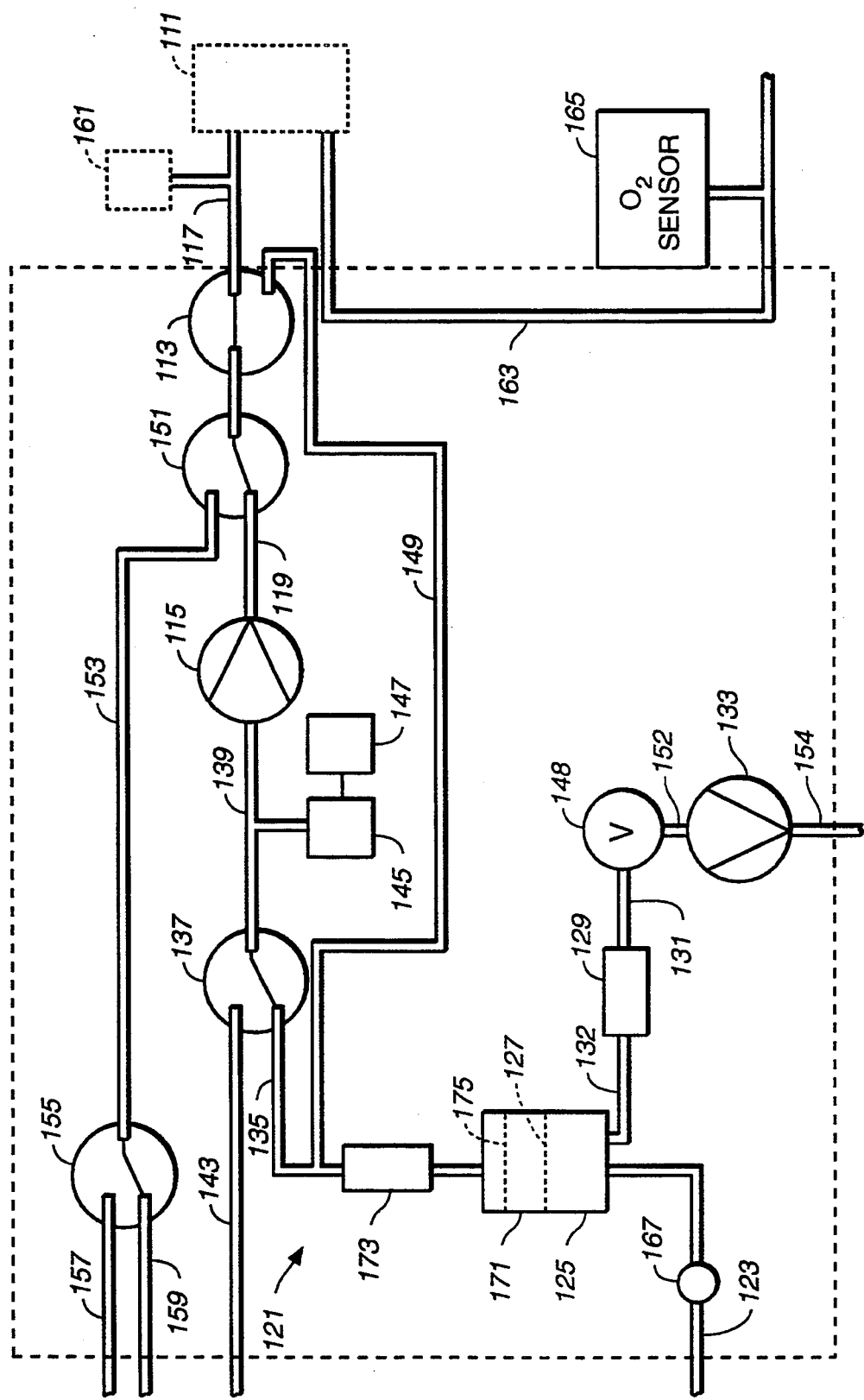
FIG._2

FILTER SYSTEM

The present invention relates to gas analyzers. More particularly, the invention relates to an improved method and system for preventing flooding of gas analyzers due to excess liquid in the inlet stream.

BACKGROUND OF THE INVENTION

Certain types of gas analyzers employ a sample cell into which gas to be analyzed is pumped. Energy is passed through the gas in the sample cell, for example using an infrared beam, and the effect on the energy is analyzed to determine the concentration of constituents of the gas in the sample cell.

A gas analyzer of the general type described above is an automotive exhaust gas analyzer. An example of an automotive exhaust gas analyzer is shown and described in U.S. Pat. No. 4,687,934. Such gas analyzers measure the presence of carbon monoxide, carbon dioxide and various hydrocarbons, which are typical constituents of automotive exhaust gas.

Engine exhaust emissions contain coarse and fine particulate matter, water in both liquid and vapor phase, other condensates, gaseous hydrocarbons, carbon monoxide, carbon dioxide, oxides of nitrogen, oxygen, and other compounds. Contaminants must be filtered out by a series of different filters, each suited for the particular contaminant in order to accurately measure the remaining constituents of the gas. The general filtration process involves first removing large particles, liquid water, and other condensates using a relatively coarse filter stage. The condensate can be filtered by another finer filter stage before being drawn off by a pump. The filtered gas can also be filtered for finer particles (typically less than 5 micron particles) by another filter stage. In particular, the removal of water before the final filter stage is important because water absorbs the hydrocarbons which is one of the classes of gases to be analyzed. If water is present in the final filter stage, the hydrocarbon measurements will be inaccurate. Further, certain structural materials can adsorb molecules to be analyzed. These adsorption phenomena can deleteriously affect the accuracy of the analyzer. Thus, the filtration process is extremely important for accurate measurements of gas constituents and to protect the analyzer and pumps.

A particularly useful filter assembly for a gas analyzer is shown and described in U.S. Pat. No. 5,049,170 Sep. 17, 1991 and assigned to the assignee of the present invention. One of the significant advantages of the filter assembly shown and described in the aforesaid patent is its relatively low void volume. This produces increased accuracy by minimizing the amount of surface area to which hydrocarbons can adhere, and requires a modest pump flowrate with attendant advantages.

The presence of large amounts of condensate, puddles of liquid in the exhaust system, careless placement of the intake probe, etc., can, on occasion, result in a large and sudden intake of liquid into a gas analyzer system. Filter assemblies which are of low volume to improve accuracy of hydrocarbon measurements, such as the filter assembly described in the above referenced patent, may become flooded or overwhelmed by the sudden intake of liquid, rendering the analyzer system inoperable. It is a general object of the invention to provide an improved filter system for a gas analyzer.

A more specific object of the invention is to provide an improved filter system for a gas analyzer which prevents the flooding or overwhelming of the gas analyzer as a result of a sudden rise in liquid intake into the filter system.

A further object of the invention is to provide an improved gas analyzer wherein flooding or overwhelming of the analyzer is prevented in a low cost and expedient manner.

Other objects of the invention will become apparent to those skilled in the art from the following description, taken in connection with the accompanying drawings.

DESCRIPTION OF DRAWINGS

FIG. 1 is a schematic diagram illustrating a general form of a system constructed in accordance with the invention.

FIG. 2 is a schematic diagram of a more specific application of the invention to a particular type of automotive exhaust gas analyzer system.

SUMMARY OF THE INVENTION

Very generally, the system of the invention prevents flooding of a gas analyzer of the type wherein a pump conveys gas to be analyzed to a sample cell and wherein a filter assembly separates water from the gas flowing to the sample cell. The presence of excess liquid in the filter assembly is sensed, and pressure in the filter assembly is increased in response to such sensing sufficiently to prevent excess inlet liquid from flooding the analyzer. The period of time during which the pressure is increased is sufficient to permit the excess liquid to pass from the filter assembly. Once the excess liquid has been eliminated, operation of the analyzer is resumed.

DETAILED DESCRIPTION OF THE INVENTION

Referring now particularly to FIG. 1, a general form of a system constructed in accordance with the invention is illustrated schematically. The sample cell 11, comprising a portion of a gas analyzer, the remainder of which is not illustrated, is filled with gas via a three way valve 13 from a pump 15. A conduit 17 connects the three way valve 13 with the sample cell 11, and a conduit 19 connects the pump output side with the three way valve 13.

A filter assembly 21 is provided, having an intake conduit 23 through which gas to be analyzed is introduced to the system. In the illustrated embodiment, the filter assembly 21 includes a gas/water separation stage 25. The gas/water separation stage 25 includes a gas filter 27 and a liquid filter 29. Gas and liquid entering the gas/liquid separation stage through the conduit 23 are separated, with the liquid passing through the filter 29 and being withdrawn from the system through a liquid drain 31 and drainage pump 33. Gas entering the gas/liquid separation stage 25 passes through the filter 27 and through the gas outlet conduit 35.

It is to be understood that the filter unit 21 may comprise several stages in addition to the gas/liquid separation stage 25, and that such additional stages are not illustrated.

The conduit 35 connects the filter unit 21 via a three way valve 37 to the pump 15. A conduit 39 connects the three way valve 37 to the pump 15. A source of gas 41 is connected to the three way valve 37 via a conduit 43. A flow sensor 45 is connected to the conduit 39 to sense the flow of fluid therein. The sensor 45 is connected to a valve control 47 which operates both the three way valve 13 and the three way valve 37. A feed back conduit 49 connects from the three way valve 13 to the conduit 35 between the pump 15 and the three way valve 37, on the one hand, and the filter unit 21 on the other.

During ordinary operation, gas and liquid entering the intake conduit 23 are drawn into the filter unit 21 and separated in the gas/liquid separation stage 25 thereof. Gas leaving the filter unit passes through the three way valve 37, the pump 15, and the three way valve 13 to the sample cell 11 for analysis.

In the event that a large amount of water enters the filter assembly 21, the presence of such a large amount of water is detected by the sensor 45. In the preferred embodiment of the invention, a flow sensor is used. Ordinarily, such a flow sensor may be employed to indicate when filters in the filter unit 21 are clogging and need replacement. Such a flow sensor will also indicate the presence of excess water by indicating a low flow condition. Such a condition typically will result in a drop in indicated flow rate of ten-fold or more.

Confirmation of this may be observed from the classical viscous flow equation (the Poiseuille equation) for a straight tube of circular cross-section as follows:

$$Q = \frac{\pi a^4 P_a(P_2 - P_1)}{8\eta l}$$

wherein $a$ is the tube radius; $l$, the tube length; $\eta$, the viscosity of the gas; and $P_a$, the arithmetic mean of $P_1$ and $P_2$; where $P_2$ is the upstream and where $P_1$ is the downstream pressure. The above equation may be simplified, for a given tube of circular cross-section to:

$$Q = \frac{K\Delta P^2}{\eta}$$

where K is a constant equal to $$\frac{\pi a^4}{16}.$$

Since the viscosity of water is 10,000 micropoise at 20° C. and is 3545 micropoise at 80° C., and since the viscosity of air is only approximately 300 micropoise, it may be seen that the presence of water results in a substantial increase in the subtend of the equation. This causes the flow sensor to indicate a low flow condition, of the order of one-tenth or less than indicated in presence of a normal flow condition. Moreover, this sensing will occur as soon as the bolus of excess water enters the system. It will be apparent to those skilled in the art that, for some system configurations, hydrostatic pressure may also affect the value of the subtend of the equation.

Upon a sensing of the presence of excess water, the valve control 47 operates to shift the three way valve 13 so that the output of the pump is shut-off from the sample cell 11 and, instead, is coupled back through the feedback conduit 49 to the conduit 35. In addition, the valve control 47 shifts the three way valve 37 so that the inlet side of the pump 15 is coupled through the conduit 43 to the source of gas 41. The result is that the pump 15 pressurizes the system and, in particular, the filter unit 21. The amount of pressurizing is sufficient to prevent the intrusion of water into the system via the conduit 23 and occurs promptly enough to prevent wetting of the filter 27. The valve control maintains such a state of the three way valves 13 and 37 for a period of time sufficient for the pump 33 to draw off the excess water from the gas/liquid filter stage 25. Once this occurs, the three way valves 13 and 37 are returned to their original condition and pumping of gas to the sample cell 11 is resumed.

The foregoing system prevents clogging by a sudden intake of water or other liquid and the resulting pressure in the filter stage 27 will prevent liquid saturation of the filter 27 and any subsequent filter stages in the filter unit 21. Switching can be accomplished in approximately one-half second, and the system may be held in the feedback mode for approximately five seconds until excess water is drawn off. If the system switches back and excess water is still present, a low flow condition will again be sensed, and the valve control 47 will re-trigger feedback operation of the three way valves 13 and 37.

Under certain conditions, continuing operation of the pump 33 may prevent sufficient pressure buildup to block water intake. This may be avoided by shutting of the pump 33 during the feedback mode of system operation. Alternatively, a valve 48 may be between the filter 29 and the pump 33. The valve 48 is closed by the valve control 47 during the feedback mode of operation. In such a case, the excess water is allowed to drain from the system by back pressure and/or gravity back out the inlet line 23 or via a suitable drain conduit, not shown.

Referring now to FIG. 2, the system of the invention is shown employed in connection with an exhaust gas analyzer such as of the type designated model 6230 available from Andros Incorporated, Berkeley, Calif., the assignee of the present invention. Components of the apparatus shown and in FIG. 2 and corresponding to components shown in FIG. 1 are given the same reference number preceded by a 1.

Thus, in FIG. 2, it may be seen that the filter unit 121 is connected via a conduit 135 to a three way valve 137. The valve 137 also is connected to the source of zero gas (not shown) via the conduit 143. The valve 137 is, in turn, connected via a conduit 139 to a pump 115. The output side of the pump 115 is connected via a conduit 119 to a three way valve 113 which, in turn, is connected via a conduit 117 to a sample cell 111. As illustrated, an additional three way valve 151 is interposed in the conduit 119 between the pump 115 and the three way valve 113. A conduit 153 connects this valve 151 to a further three way valve 155. The valve 155 is connected via a conduit 157 to a source of high end calibration gas and is connected via a conduit 159 to a source of low end calibration gas. The calibration gases are used in calibrating the unit, with the pump turned off and three way valve 151 connecting the conduit 153 via the three way valve 113 to the sample cell 111.

Additional elements in the system of FIG. 2 include a pressure transducer 161 connected to the conduit 117, an outlet conduit 163 for the sample cell to vent exhaust gas from the system, and an oxygen sensor 165 connected to the conduit 163. Additionally, a flow restrictor 167 is positioned in the sample inlet conduit 123.

As illustrated in FIG. 2, the filter unit 121 includes additional filter stages. Thus, in addition to the filter stage 125 wherein gas and liquid are separated, an additional filter stage 171 is provided for faltering gas and a further filter stage 173 is also provided for filtering gas. In the preferred embodiment, the filter stage 125 includes a 48 micron filter 127 and the filter stage 171 includes an 8 micron filter 175. The filter stage 173 includes a 10 micron filter therein. The feedback conduit 149 is connected from the three way valve 113 to the conduit 135 between the filter stage 173 and the three way valve 137.

In the illustrated embodiment of FIG. 2, when flow restriction is sensed by the pressure sensor 145, the valve control 147 switches the solenoid controlled valve 137 from the position shown to the position in which zero gas is introduced to the system. At the same time, the solenoid or three way valve 113 is switched to feed back the output of the pump 115 to the conduit 135. The pump 133 is then able to pump off any water present in the probe line 123 and in the gas/liquid separating stage 125. As illustrated in FIG. 2, interposed between pump 133 and probe line 123 are filter stage 125, an additional filter 129 and valve 148. Filter stage 125 is connected to filter 129 via conduit 132 which, in turn, is connected to valve 148 via conduit 131. Valve 148 is connected to pump 133 via conduit 152.

A suitable drain conduit 154 to drain the excess water is also provided. The drain conduit 154 is operatively connected to pump 133.

It may be seen, therefore, that the invention provides an improved filter system for a gas analyzer wherein flooding or overwhelming of the analyzer by a sudden rise in liquid intake is prevented in a low cost and expedient manner. The system is thus protected from careless use or other inadvertent intake of liquid into the system.

Various modifications of the invention in addition to those shown and described herein will become apparent to those skilled in the art from the foregoing description and accompanying drawings. Such modifications are intended to fall within the scope of the appended claims.

What is claimed is:

1. A method for preventing flooding of a gas analyzer of the type wherein a pump conveys gas to be analyzed from a filter system to a sample cell, and wherein the system includes a gas/water separation filter stage which separates water from the gas flowing to the pump, said method comprising, sensing the presence of excess liquid in said filter system, and increasing pressure in said filter system subsequent to said gas/liquid separation stage and prior to the sample cell sufficiently to prevent excess inlet liquid from flooding the gas analyzer, said pressure being increased for a predetermined period of time sufficient to permit the excess liquid to pass from said filter system via said gas/liquid separating stage.

2. A method according to claim 1 wherein said sensing step is performed by sensing a drop in flow rate to said pump in excess of ten-fold, and wherein the output of said pump is diverted from said sample cell to said filter system.

3. A method according to claim 1 wherein during the pressurizing step, said inlet of said pump is decoupled from said filter system and is coupled to a clean gas source.

4. A method according to claim 3 wherein said clean gas source is a source of zeroing gas for the gas analyzer.

5. A gas analyzer system comprising:
a sample cell for containing gas to be analyzed;
a pump having an output side connected to said sample cell for conveying gas to said sample cell, and having an inlet side;
a filter assembly connected to said inlet side of said pump for filtering gas to be sampled prior to conveyance by said pump to said sample cell;
said filter assembly including a gas/liquid separating stage wherein liquid is separated from the gas to be sampled;
sensor means for sensing the presence of excess liquid in said filter assembly;
and pressurizing means controlled by said sensor means for increasing the pressure in said filter assembly subsequent to said gas/liquid separating stage and prior to the sample cell sufficiently to prevent excess inlet liquid from flooding said filter assembly, said pressurizing means increasing the pressure for a predetermined period of time sufficient to permit the excess liquid to pass from said filter assembly via said gas/liquid separating stage.

6. A gas analyzer system according to claim 5 wherein said pressurizing means includes means for connecting the outlet of said pumping means to said filter assembly for increasing the pressure therein.

7. A gas analyzer system according to claim 6 including means for disconnecting said inlet side of said pumping means from said filter assembly and connecting it to a gas source for said predetermined period of time.

8. A gas analyzer system according to claim 7 wherein said gas source comprises a source of zero gas for zeroing the gas analyzer.

9. A gas analyzer system according to claim 6 including further pumping means connected to said gas/liquid separating stage for removing separated water therefrom, and including valve means between said further pumping means and said gas/liquid separating stage, said valve means operating to a closed position during said predetermined period of time.

10. A gas analyzer system according to claim 5 wherein said sensor means comprise a flow transducer.

11. A gas analyzer system according to claim 5 wherein said filter assembly comprises a plurality of filter stages, and wherein said pressurizing means is coupled between the last of said filter stages and said pumping means.

12. A filter system for a gas analyzer employing a sample cell, said filter system including gas/liquid separating means for separating inlet gas and liquid prior to passage of gas to the sample cell for analysis, sensor means for sensing the presence of excess liquid in said filter system, and pressurizing means operable in response to the sensing of excess liquid for increasing the pressure in said filter system subsequent to said gas/liquid separating means and prior to the sample cell sufficiently to prevent excess inlet liquid from flooding the gas analyzer, said pressurizing means increasing the pressure in said filter system for a predetermined period of time sufficient to permit the excess liquid to pass from said filter system via said gas/liquid separating stage.

13. A filter system according to claim 12 wherein the gas analyzer includes gas pumping means having an inlet and an outlet for pumping gas from said filter system to the sample cell, and wherein said pressurizing means include means for connecting said outlet of said pumping means to said filter system for increasing the pressure therein.

14. A filter system according to claim 13 including a gas source and means for disconnecting said inlet of the pumping means from said filter system and connecting said inlet to said gas source for the predetermined period of time.

15. A filter system according to claim 14 wherein gas source comprises a source of zero gas for zeroing the gas analyzer.

16. A filter system according to claim 13 wherein said filter system comprises a plurality of filter stages in succession, and wherein said pressurizing means is coupled between the last of said filter stages and said pumping means.

17. A filter system according to claim 13 including further pumping means connected to said gas/liquid separating stage for removing separated water therefrom, and including valve means between said further pumping means and said gas/liquid separating stage, said valve means operating to a closed position during said predetermined period of time.

18. A filter system according to claim 12 wherein said sensor means comprises a flow pressure transducer.

* * * * *